(12) United States Patent
Gallem et al.

(10) Patent No.: US 10,245,391 B2
(45) Date of Patent: Apr. 2, 2019

(54) FLUID RESERVOIR FOR AN AEROSOL GENERATION DEVICE, COMBINATION OF FLUID RESERVOIR AND PRIMARY FLUID PACKAGE, AND AEROSOL GENERATION DEVICE FOR USE WITH THE FLUID RESERVOIR

(71) Applicant: PARI Pharma GmbH, Starnberg (DE)

(72) Inventors: Thomas Gallem, München (DE); Uwe Hetzer, München (DE); Michael Neuner, München (DE)

(73) Assignee: PARI Pharma GmbH, Starnberg (DE)

( * ) Notice: Subject to any disclaimer, the term of this patent is extended or adjusted under 35 U.S.C. 154(b) by 896 days.

(21) Appl. No.: 14/442,441

(22) PCT Filed: Nov. 5, 2013

(86) PCT No.: PCT/EP2013/073010
§ 371 (c)(1),
(2) Date: May 13, 2015

(87) PCT Pub. No.: WO2014/082818
PCT Pub. Date: Jun. 5, 2014

(65) Prior Publication Data
US 2016/0279351 A1 Sep. 29, 2016

(30) Foreign Application Priority Data

Nov. 27, 2012 (EP) ..................... 12194385

(51) Int. Cl.
*A61M 11/00* (2006.01)
*A61M 15/00* (2006.01)
*A61M 16/16* (2006.01)

(52) U.S. Cl.
CPC .......... *A61M 11/005* (2013.01); *A61M 15/00* (2013.01); *A61M 15/0003* (2014.02);
(Continued)

(58) Field of Classification Search
CPC .... A61M 11/005; A61M 16/16; A61M 15/00; A61M 15/0028; A61M 15/0003;
(Continued)

(56) References Cited

U.S. PATENT DOCUMENTS 5,147,054 A * 9/1992 Pehr ................... B65D 47/0842
215/232
6,280,410 B1 8/2001 Weston et al.
(Continued)

FOREIGN PATENT DOCUMENTS

CN 2178692 Y 10/1994
CN 1285762 A 2/2001
(Continued)

OTHER PUBLICATIONS

Chinese Examination Report dated Jan. 22, 2017 in connection with Chinese Application No. 201380061793.1.

*Primary Examiner* — Steven O Douglas
(74) *Attorney, Agent, or Firm* — Wolf, Greenfield & Sacks, P.C.

(57) ABSTRACT

A fluid reservoir is attachable to an aerosol generation device for guiding a fluid from a fluid container to the aerosol generation device. The fluid reservoir has an interface portion arranged at the fluid reservoir for attaching the fluid reservoir to the aerosol generation device. The interface portion has a locking element configured to non-detachably lock the fluid reservoir to the aerosol generation device after attachment of the fluid reservoir to the aerosol generation device. The locking element is breakable to enable detachment of the fluid reservoir from the aerosol generation device. A combination includes the fluid reservoir and a primary fluid package, wherein the primary fluid package has at least one chamber containing a fluid therein. An aerosol generation device is configured for use with the fluid
(Continued)

reservoir has an attachment portion for receiving the interface portion of the fluid reservoir.

14 Claims, 7 Drawing Sheets

(52) U.S. Cl.
CPC ........ *A61M 15/0028* (2013.01); *A61M 16/16* (2013.01); *A61M 2202/0468* (2013.01); *A61M 2202/064* (2013.01); *A61M 2205/273* (2013.01); *A61M 2205/276* (2013.01)

(58) Field of Classification Search
CPC .... A61M 2205/276; A61M 2202/0468; A61M 2205/273; A61M 2202/064
See application file for complete search history.

(56) References Cited

U.S. PATENT DOCUMENTS

| | | | | |
|---|---|---|---|---|
| 6,948,491 | B2 * | 9/2005 | Loeffler | A61M 15/0028 |
| | | | | 128/200.14 |
| 6,968,840 | B2 * | 11/2005 | Smith | A61J 1/065 |
| | | | | 128/200.14 |
| 2002/0043547 | A1 | 4/2002 | Shkolnikov et al. | |
| 2002/0129812 | A1 | 9/2002 | Litherland et al. | |
| 2002/0134372 | A1 | 9/2002 | Loeffler et al. | |
| 2003/0140921 | A1 | 7/2003 | Smith et al. | |
| 2006/0057257 | A1 * | 3/2006 | Ma | B65D 41/3428 |
| | | | | 426/115 |
| 2006/0213505 | A1 | 9/2006 | Hodson et al. | |
| 2009/0281485 | A1 * | 11/2009 | Baker | A61M 1/0058 |
| | | | | 604/35 |
| 2009/0293868 | A1 | 12/2009 | Hetzer et al. | |
| 2010/0269818 | A1 | 10/2010 | Abrams | |
| 2011/0045088 | A1 | 2/2011 | Tsutsui et al. | |
| 2011/0146670 | A1 | 6/2011 | Gallem et al. | |
| 2013/0133643 | A1 | 5/2013 | Hodson et al. | |

FOREIGN PATENT DOCUMENTS

| | | |
|---|---|---|
| CN | 1418759 A | 5/2003 |
| CN | 101291699 A | 10/2008 |
| WO | WO 99/025407 A1 | 5/1999 |
| WO | WO 00/015281 A1 | 3/2000 |
| WO | WO 03/059424 A1 | 7/2003 |
| WO | WO 09/111612 A1 | 9/2009 |
| WO | WO 11/088070 A1 | 7/2011 |

* cited by examiner

Fig. 5(a)
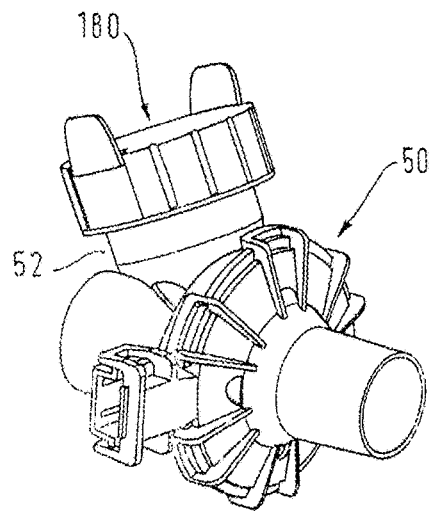
Fig. 5(b)
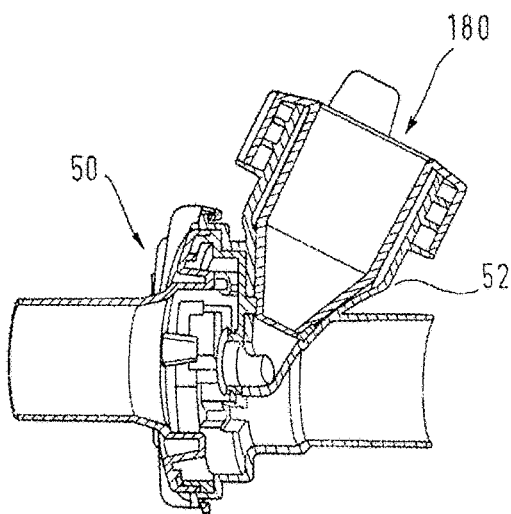
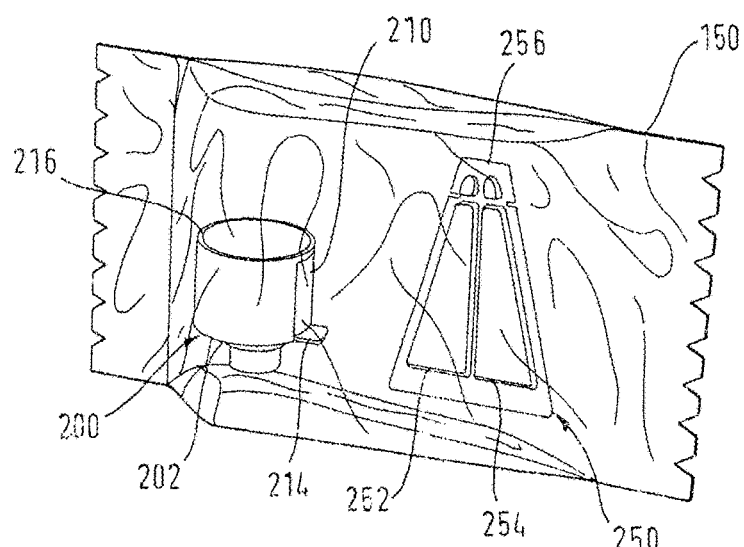
Fig. 6

FLUID RESERVOIR FOR AN AEROSOL GENERATION DEVICE, COMBINATION OF FLUID RESERVOIR AND PRIMARY FLUID PACKAGE, AND AEROSOL GENERATION DEVICE FOR USE WITH THE FLUID RESERVOIR

CROSS REFERENCE TO RELATED APPLICATIONS

This application is a national stage of PCT/EP2013/073010, filed Nov. 5, 2013, which claims priority to European Patent Application No. 12194385.6, filed Nov. 27, 2012, which are hereby incorporated herein by reference in their entirety.

FIELD OF THE INVENTION

The invention relates to a fluid reservoir which is attachable to an aerosol generation device (nebuliser) for guiding a fluid from a fluid container to the aerosol generation device, a combination of the fluid reservoir and a primary fluid package and an aerosol generation device which is configured for use with the fluid reservoir.

BACKGROUND ART

Aerosols for therapeutic purposes are generated with aerosol generation devices. A conventional aerosol generation device is disclosed, for example, in US-A-2011/0146670. The aerosol generation device of this document comprises a fluid reservoir for receiving a fluid (i.e., medicament) to be nebulised, which is connected to the body of the device. The fluid reservoir may be integrally connected to the device. Alternatively, the fluid reservoir may be connected to the device in such a manner that it can be coupled to and uncoupled from the device.

Aerosols for therapeutic purposes generally have to meet high requirements with regard to purity. Hence, if a fluid reservoir that had been previously used for receiving a first fluid is to be reused with a second, different fluid, the reservoir has to be thoroughly cleaned. However, for some fluids even such a thorough cleaning procedure is not sufficient. In this case, the used fluid reservoir has to be discarded and a new fluid reservoir has to be used.

Nevertheless, there remains a risk that a used fluid reservoir is accidentally reused, potentially causing a contamination of the aerosol, thereby reducing the effectiveness of the aerosol treatment or even posing a health risk to a patient receiving the aerosol treatment.

US-A-2006/0213505 discloses an actuator for an inhaler for delivering a medicament by inhalation, comprising: a main body comprising a tubular member for receiving a canister containing the medicament and having a valve stem extending therefrom, a bottom surface at one end of the tubular member, a mouthpiece for guiding the medicament to the mouth of a user, and a nozzle block located in the bottom region of the tubular member for receiving the valve stem of the canister and delivering the medicament from the canister into the mouthpiece.

SUMMARY OF THE INVENTION

One object of the invention is to provide a fluid reservoir which is attachable to an aerosol generation device for guiding a fluid from a fluid container to the aerosol generation device, allowing for an accidental reuse of the fluid reservoir to be reliably prevented, thus minimising the risk of contamination of the generated aerosol. Further, the invention aims to provide a combination of the fluid reservoir and a primary fluid package and an aerosol generation device which is configured for use with the fluid reservoir.

These goals are achieved by a fluid reservoir with the technical features of claim 1, a combination of the fluid reservoir and a primary fluid package with the technical features of claim 10 and an aerosol generation device with the technical features of claim 12.

The invention provides a fluid reservoir which is attachable to an aerosol generation device for guiding a fluid from a fluid container to the aerosol generation device. The fluid reservoir has an interface portion arranged at the fluid reservoir for attaching the fluid reservoir to the aerosol generation device. The interface portion has a locking element (safety lock element or closing seal element) configured to non-detachably lock the fluid reservoir to the aerosol generation device after attachment of the fluid reservoir to the aerosol generation device. The locking element is breakable to enable detachment of the fluid reservoir from the aerosol generation device, while reattachment to the aerosol generation device may be disabled. The locking element may be configured so that, after breaking thereof, reattachment of the fluid reservoir to the aerosol generation device is disabled.

The fluid reservoir may comprise the fluid container. The interface portion may be arranged at an end of the fluid reservoir.

The locking element is configured so that, after attachment of the fluid reservoir to the aerosol generation device, the fluid reservoir cannot be detached from the aerosol generation device without breaking the locking element.

Hence, the fluid reservoir is damaged after detachment thereof from the aerosol generation device, i.e., after its use. Therefore, an accidental reuse of the fluid reservoir is reliably prevented, thus minimising any risk of contamination of the aerosol and ensuring an effective aerosol treatment.

The fluid reservoir may be configured so that the breaking of the locking element destroys the fluid reservoir, i.e., renders it unusable. In particular, the locking element may be configured so that, after breaking thereof, the fluid reservoir is no longer attachable to the aerosol generation device. In this way, an accidental reuse of the fluid reservoir can be prevented in a particularly reliable manner.

The locking element may be configured so that the breaking thereof leaves visible traces in the fluid reservoir. These traces will alarm a user that the fluid reservoir had been used before. Thus, in this case, the locking element of the interface portion may act as a tamper-evident feature.

The locking element may be configured to initially non-detachably lock the fluid reservoir to the aerosol generation device after attachment of the fluid reservoir to the aerosol generation device. Herein, the term "initially" defines that the locking element is configured to non-detachably lock the fluid reservoir to the aerosol generation device in an initial state, i.e., in a state in which the locking element is intact, i.e., has not been broken.

The interface portion of the fluid reservoir may comprise one or more attachment elements, such as pins or bolts, e.g., detent pins or index bolts, enabling attachment of the fluid reservoir to the aerosol generation device. The one or more attachment elements may be configured so that they can be brought into engagement with an attachment portion, such as a thread, threaded splines, a bayonet coupling or the like, of the aerosol generation device.

The locking element of the interface portion of the fluid reservoir may cooperate or interact with the one or more attachment elements so that breaking the locking element enables the one or more attachment elements to be disengaged from the attachment portion of the aerosol generation device. For example, the locking element may comprise one or more flaps, tabs, lugs or the like arranged on the interface portion and connected to the one or more attachment elements, so that pulling or pressing these flaps, tabs, lugs etc. breaks the locking element and brings the at least one attachment element out of engagement with the attachment portion of the aerosol generation device, thus enabling detachment of the fluid reservoir from the device.

Further, the locking element may be configured so that the breaking thereof allows for the one or more attachment elements to be removed from the interface portion of the fluid reservoir, thereby enabling detachment of the fluid reservoir from the device.

Beside the locking element, the interface portion may have a sealing element configured to seal (plug, connect, drain off) the fluid reservoir to the aerosol generation device after attachment of the fluid reservoir to the aerosol generation device. Therefore, a fluid can be guided without losses or leak to the aerosol generation device.

The sealing element may comprise an elastic material, like silicone, rubber, soft plastic and so on. The sealing element may be formed as a gasket, a joint ring, a lip seal or the like to connect the fluid reservoir with the sealing element to the aerosol generation device.

The fluid reservoir may be formed of one or more parts. The fluid reservoir may comprise the fluid container and an adapter. The fluid container and the adapter may act together as a fluid reservoir. In this case, the fluid is guided by the adapter from the fluid reservoir to the aerosol generation device. The adapter and/or the fluid container may comprise one or more locking elements and/or sealing elements as described above.

The adapter may have the interface portion of the fluid reservoir for attaching the fluid reservoir to the aerosol generation device.

Herein, the term "fluid container" refers to any type of container in which a fluid, e.g., a fluid containing a medicament or active compound, can be stored. The fluid container may be made of various materials, for example, plastic, such as polypropylene, glass, ceramic, metal or other suitable materials. For example, if the fluid container is made of plastic, it can be manufactured in a particularly simple manner, e.g., by injection moulding, a blow-fill-seal process and the like.

The fluid container may be formed of one or more parts. The fluid container may comprise one fluid chamber for containing a fluid therein or a plurality of fluid chambers for containing the same type or different types of fluid therein.

The fluid container may comprise two or more chambers with solid substance, powder and/or fluid, which could be mixed in the fluid container and/or in the fluid reservoir, e.g., directly before the use of the aerosol generation device. A fluid mixture of the same kind is for example "Colistin" or "Asperin".

The fluid container may have a substantially cylindrical shape. Alternatively, the fluid container may have a rectangular, square, triangular or other polygonal cross-sectional shape.

The fluid container may comprise a base portion which allows for the container to be placed on a flat surface. In this case, the container can be filled with a fluid in a particularly simple and convenient manner, for example from a primary fluid package, a vial or the like.

The fluid container may be rigid in shape or flexible or collapsible, e.g., in the form of a blister or pouch.

Further, also the fluid reservoir may be made of various materials, such as plastic, e.g. polypropylene, glass, ceramic, metal or other suitable materials. In particular, the fluid reservoir may consist of different or same materials in sections or in combinations, like sandwich materials.

The fluid reservoir of the invention may be used with any type of aerosol generation device, aerosol delivery device, aerosol inhalation device, medical aerosol device, aerosol diagnostic device, aerosol prophylactic device, aerosol therapeutic device, aerosol humidification device, a humidifier/nebuliser for ventilation devices, or aerosol therapy device. In particular, the aerosol generation device may be a nebuliser, an atomiser, such as a humidifier, a pneumatic nebuliser, a jet nebuliser, an electronic nebuliser, an ultrasonic nebuliser, an electro-hydrodynamic nebuliser, an electrostatic nebuliser, a membrane nebuliser, a vibrating membrane nebuliser, e.g., an electronic vibrating membrane nebuliser, or the like.

The fluid to be guided from the fluid reservoir, with and without an adapter, to the aerosol generation device may be a fluid for the generation of a pharmaceutical aerosol for the delivery of an active compound. An active compound is a natural, biotechnology-derived or synthetic compound or mixture of compounds useful for the diagnosis, prevention, management and/or treatment of a disease, condition or symptom of an animal, in particular, a human.

Other terms which may be used as synonyms of the term "active compound" include, for example, active ingredient, active pharmaceutical ingredient, drug substance, diagnostic material, drug, medicament or the like. The fluid can be of a liquid, reconstructed solid substance or powder, solution, suspension, nano-suspension, colloidal mixture or liposomal formulation form.

The fluid reservoir of the invention is particularly advantageous for use with multi-component fluids, in which two or more components of the fluid have to be mixed immediately before the aerosol treatment. The multi-component fluids may be a mixture of fluid and fluid, of fluid and powder as well as of fluid and solid substance. Generally, such multi-component fluids are especially sensitive to contaminations in the fluid reservoir or the aerosol generation device.

The active compound or compounds comprised in the fluid to be guided from the fluid reservoir, with or without an adapter, to the aerosol generation device may be a drug substance or a medicament which is useful for the prevention, management, diagnosis or treatment of any disease, symptom or condition affecting the body, the skin, the body cavities, the abdomen, the eyes, the intestine, the stomach, the nose, the sinuses, the osteomeatal complex, the mouth, the trachea, the lungs, the bronchia, the bronchioles, the alveoli and/or the respiratory tract.

Among the active compounds which may be useful for serving one of the purposes named previously and that may be used together with the present invention are, for example, substances selected from the group consisting of anti-inflammatory compounds, anti-infective agents, antiseptics, prostaglandins, endothelin receptor agonists, phosphodiesterase inhibitors, beta-2-sympathicomimetics, decongestants, vasoconstrictors, anticholinergics, immunomodulators, mucolytics, anti-allergic drugs, antihistaminics, mast-cell stabilizing agents, tumor growth inhibitory agents, wound healing agents, local anaesthetics, antioxidants, oligonucleotides, peptides, proteins, vaccines, vitamins, plant extracts, cholinesterase inhibitors, vasoactive intestinal peptide, serotonin receptor antagonists, and heparins, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anaesthetics, oligonucleotides, xanthin derived agents, peptides, proteins and plant extracts. Such compound may be used in the form of a liquid, a powder, a solid substance, a suspension, a solution, a colloidal formulation (i.e., liposomal), etc. as well as a mixture thereof.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluoconolone acetonide, fluocinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate (DHEAS), elastane, prostaglandin, leukotriene, bradykinin antagonists, non-steroidal anti-inflammatory drugs (NSAIDs), such as ibuprofen including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillins (mecillinam);

cephalosporins, including cefazolins (cefazolin, cefazedone); cefuroximes (cefuroxim, cefamandole, cefotiam); cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole;

synergists, including beta-lactamase inhibitors, such as clavulanic acid, sulbactam, and tazobactam;

carbapenems, including imipenem, cilastin, meropenem, doripenem, tebipenem, ertapenem, ritipenam, and biapenem;

monobactams, including aztreonam;

aminoglycosides, such as apramycin, gentamicin, amikacin, isepamicin, arbekacin, tobramycin, netilmicin, spectinomycin, streptomycin, capreomycin, neomycin, paromoycin, and kanamycin;

macrolides, including erythromycin, clarythromycin, roxithromycin, azithromycin, dithromycin, josamycin, spiramycin and telithromycin;

gyrase inhibitors or fluoroquinolones, including ciprofloxacin, gatifloxacin, norfloxacin, ofloxacin, levofloxacin, perfloxacin, lomefloxacin, flerofloxacin, garenoxacin, clinafloxacin, sitafloxacin, prulifloxacin, olamufloxacin, caderofloxacin, gemifloxacin, balofloxacin, trovafloxacin, and moxifloxacin;

tetracyclins, including tetracyclin, oxytetracyclin, rolitetracyclin, minocyclin, doxycycline, tigecycline and aminocycline;

glycopeptides, inlcuding vancomycin, teicoplanin, ristocetin, avoparcin, oritavancin, ramoplanin, and peptide 4;

polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides, including sulfadiazine, sulfamethoxazole, sulfalene, co-trimoxazole, co-trimetrol, co-trimoxazine, and co-tetraxazine;

azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofulvin, tolnaftal, naftifin, terbinafin, amorolfin, ciclopiroxolamin, echinocandins, such as micafungin, caspofungin, anidulafungin;

nitrofurans, including nitrofurantoin and nitrofuranzone;

polyenes, including amphotericin B, natamycin, nystatin, flucytosine;

other antibiotics, including tithromycin, lincomycin, clindamycin, oxazolindiones (linzezolids), ranbezolid, streptogramine A+B, pristinamycin A+B, Virginiamycin A+B, dalfopristin /quinupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine;

antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors, siRNA based drugs;

antiseptics, including acridine derivatives, iodine-povidone, benzoates, rivanol, chlorhexidine, quarternary ammonium compounds, cetrimides, biphenylol, clorofene, and octenidine;

plant extracts or ingredients, such as plant extracts from chamomile, hamamelis, echinacea, calendula, thymian, papain, pelargonium, pine trees, essential oils, myrtol, pinen, limonen, cineole, thymol, mentol, camphor, tannin, alpha-hederin, bisabolol, lycopodin, vitapherole;

wound healing compounds including dexpantenol, allantoin, vitamins, hyaluronic acid, alpha-antitrypsin, anorganic and organic zinc salts/compounds, salts of bismuth and selen;

interferones (alpha, beta, gamma), tumor necrosis factors, cytokines, interleukines;

immunmodulators including methotrexat, azathioprine, cyclosporine, tacrolimus, sirolimus, rapamycin, mofetil; mofetil-mycophenolate.

cytostatics and metastasis inhibitors;

alkylants, such as nimustine, melphanlane, carmustine, lomustine, cyclophosphamide, ifosfamide, trofosfamide, chlorambucil, busulfane, treosulfane, prednimustine, thiotepa;

antimetabolites, e.g. cytarabine, fluorouracil, methotrexate, mercaptopurine, tioguanine;

alkaloids, such as vinblastine, vincristine, vindesine;

antibiotics, such as alcarubicine, bleomycine, dactinomycine, daunorubicine, doxorubicine, epirubicine, idarubicine, mitomycine, plicamycine;

complexes of transition group elements (e.g. Ti, Zr, V, Nb, Ta, Mo, W, Pt) such as carboplatinum, cis-platinum and metallocene compounds such as titanocendichloride;

amsacrine, dacarbazine, estramustine, etoposide, beraprost, hydroxycarbamide, mitoxanthrone, procarbazine, temiposide;

paclitaxel, gefitinib, vandetanib, erlotinib, poly-ADP-ribose-polymerase (PRAP) enzyme inhibitors, banoxantrone, gemcitabine, pemetrexed, bevacizumab, ranibizumab. Examples of potentially useful mucolytics are DNase, P2Y2-agonists (denufosol), drugs affecting chloride and sodium permeation, such as N-(3,5-Diamino-6-chloropyrazine-2-carbony)-N'-{4-[4-(2,3-dihydroxypropoxy) -phenyl]buty}guanidine methanesulfonate (PARION 552-02), heparinoids, guaifenesin, acetylcysteine, carbocysteine, ambroxol, bromhexine, tyloxapol, lecithins, myrtol, and recombinant surfactant proteins.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil, cetrizin, loratidin, montelukast, roflumilast, ziluton, omalizumab, heparinoids and other antihistamins, including azelastine, cetirizin, desloratadin, ebastin, fexofenadin, levocetirizin, loratadin.

Examples of potentially useful anticholinergic agents include ipratropium bromide, tiotropium bromide, oxitropium bromide, glycopyrrolate.

Examples of potentially useful beta-2-sympathicomimetic agents include salbutamol, fenoterol, formoterol, indacaterol, isoproterenol, metaproterenol, salmeterol, terbutaline, clenbuterol, isoetarine, pirbuterol, procaterol, ritodrine.

Examples of xanthine derived agents include theophylline, theobromine, caffeine.

Antisense oligonucleotides are short synthetic strands of DNA (or analogs) that are complimentary or antisense to a target sequence (DNA, RNA) designed to halt a biological event, such as transcription, translation or splicing. The resulting inhibition of gene expression makes oligonucleotides dependent on their composition useful for the treatment of many diseases and various compounds are currently clinically evaluated, such as ALN-RSVO1 to treat the respiratory syncytical virus by, AVE-7279 to treat asthma and allergies, TPI-ASM8 to treat allergic asthma, 1018-ISS to treat cancer.

Examples of potentially useful peptides and proteins include antibodies against toxins produced by microorganisms, antimicrobial peptides such as cecropins, defensins, thionins, and cathelicidins.

The fluid reservoir of the invention may be particularly advantageously used with an aerosol generation device and a ventilator which are intended and configured to remain in connection with a patient for an extended period of time, allowing for the repeated delivery of the same or different types of aerosols. In this case, the accidental reuse of a fluid reservoir, which had been previously used for the delivery of a first type of fluid, for delivering a second type of fluid can be reliably prevented. The attachment and detachment of the fluid reservoir to and from the aerosol generation device, respectively, allows the aerosol generation device to stay in the ventilator circuit so as to avoid an opening of the breathing circle tubes. The aerosol generation device can remain in the ventilator circle and therefore could be named "Inline" aerosol generation device or nebuliser. The ventilator in this case may be a respirator, intensive care unit, high frequency jet ventilator, breathing assistance device, respiratory assistant device, RADs, C-PAP, BI-PAP, V-PAP, NVPP, controlled inhalation device (e.g., AKITA) or so on.

In one embodiment, the fluid reservoir is formed of a plurality of parts. The fluid reservoir may comprise two, three or more components. The fluid reservoir may comprise the fluid container and an adapter, such as that described above, and the fluid container may be detachably attached to an interface portion of the adapter. In this case, the adapter may be attachable to an aerosol generation device for guiding a fluid from the fluid container to the aerosol generation device.

In particular, the adapter may have the interface portion of the fluid reservoir for attaching the fluid reservoir to the aerosol generation device. The adapter may have two or more interface portions arranged at different positions (ends) of the adapter. The adapter may have a first interface portion arranged at a first end of the adapter for attaching the adapter to the aerosol generation device and a second interface portion arranged at a second end of the adapter for attaching the adapter to the fluid container. The second end of the adapter may be arranged so that it lies opposite to the first end of the adapter.

For example, the second interface portion of the adapter may be provided with a threaded section, a bayonet coupling or the like for attachment to the fluid container. The fluid container may be configured so that it cannot be attached to the aerosol generation device without the adapter.

In the embodiment detailed above, the fluid container may be filled with a fluid or a combination or mixture of different fluids, for example from one or more primary fluid packages. Subsequently, the adapter may be attached to the fluid container. In this case, the adapter and the fluid container in combination may form a fluid tight space containing the fluid or mixture of fluids and work as a fluid reservoir. The fluid container having the adapter attached thereto can be attached to the aerosol generation device for guiding the fluid from the fluid container to the device.

After delivery of the fluid to the aerosol generation device, the fluid reservoir can be detached from the device only if the locking element is broken, so that an accidental reuse of the fluid reservoir in a following aerosol treatment is reliably prevented.

The fluid container may be provided together with the adapter, e.g., so that the adapter and the fluid container are arranged together in a single package, or together with the aerosol generation device, e.g., so that the aerosol generation device and the fluid reservoir (fluid container and adapter) are arranged together in a single package.

In another embodiment, the fluid container and/or the adapter is formed integrally with the fluid reservoir. Due to this integral structure, it can be ensured that the fluid container and/or the adapter have to be discarded together with the fluid reservoir after the first use thereof. Specifically, a fluid reservoir, including a fluid container and an adapter, which has been detached from the aerosol generation device has a broken locking element, preventing an accidental reuse of the fluid reservoir and also of the fluid container and/or the adapter which is integrally formed therewith. Thus, also any contamination of the fluid container and/or the adapter can be reliably and efficiently prevented.

This integral fluid reservoir, including the fluid container and the adapter, may be made of plastic, such as polypropylene, and can be manufactured, for example, by injection moulding. In this way, the integral fluid reservoir can be fabricated in a particularly simple manner.

The fluid reservoir may further comprise a lid element for sealing the fluid reservoir or the fluid container. In this case, the fluid reservoir or the fluid container may be filled with a fluid or a combination or mixture of different fluids and the reservoir or the container may subsequently be sealed by the lid element, in order to prevent any contamination of the fluid or mixture of fluids due to contact with the surrounding environment.

The lid element may be configured so that, after sealing the fluid reservoir or the fluid container, the lid element cannot be detached from its sealing position without breaking the lid element, the fluid reservoir and/or the fluid container. In this way, a reopening of the fluid reservoir or the fluid container after it has been filled, causing the risk of contamination of the fluid or mixture of fluids contained therein, can be reliably prevented. Further, if a sealed fluid reservoir or fluid container is opened by accident, the lid element, the fluid reservoir and/or the fluid container will be broken, providing a clear indication to a user of the reopening of the reservoir or container, thus acting as a tamper-evident feature.

In one embodiment, the locking element is configured so that it has to be manually broken before detachment of the fluid reservoir from the aerosol generation device. Herein, the term "manually" means directly, i.e., by the direct application of a manual force. The locking element has to be broken first, e.g., by pulling or pressing one or more tabs, flaps, lugs or the like arranged on the interface portion of the fluid reservoir, as detailed above, in order to enable detachment of the fluid reservoir from the aerosol generation device. No detachment of the fluid reservoir from the aerosol generation device is possible before the locking element is manually broken.

This configuration of the locking element has the advantage that the requirement of manually breaking the locking element will directly indicate to a user the disposable nature of the fluid reservoir and may prompt him to discard the fluid reservoir immediately after use or at the latest before reuse.

The locking element may be configured so that the locking element is automatically broken when detaching the fluid reservoir from the aerosol generation device. Thus, the process of detaching the fluid reservoir from the device automatically breaks the locking element. Herein, the term "automatically" means that no separate action is required to break the locking element, but that the locking element is broken in the detachment process of the fluid reservoir.

Breaking the locking element may provide audible or visual feedback to the operator, caregiver or patient that the fluid reservoir and/or fluid container are no longer usable.

In this case, since no separate step of breaking the locking element is required, the fluid reservoir can be detached from the aerosol generation device in a particularly simple manner.

One or more interface portions of the fluid reservoir, the fluid container, the adapter and/or the aerosol generation device may further have one or more valve elements for regulating fluid flow from the fluid reservoir into the aerosol generation device.

In particular, the interface portion of the fluid reservoir for attaching the fluid reservoir to the aerosol generation device may have a valve element for sealing an end of the fluid reservoir and regulating the fluid flow to the aerosol generation device. The valve element may be configured so that it can be opened by a corresponding opening element, such as a thorn, a hollow needle, a collar, a conduit or the like, provided in the aerosol generation device.

By using a valve element for regulating fluid flow from or through the fluid reservoir, the fluid flow can be controlled in a particularly accurate and precise manner, thus enabling aerosol delivery with a high degree of precision. The valve element may be configured so that it is normally, i.e., if no external force is applied thereto, in a closed state, thus, for example, sealing the end of the fluid reservoir. The valve element may be, for example, a ball valve, a valve diaphragm or the like.

The interface portion of the fluid reservoir for attaching the fluid reservoir to the aerosol generation device may further have a wall element (septum) sealing an end of the fluid reservoir. The wall element may have at least one weakened portion, such as a predetermined breaking point or line or a pull linkage, facilitating at least partial breaking of the wall element. In this case, the wall element may be at least partially broken by an opening element of the aerosol generation device, such as a thorn, a hollow needle, a collar, a conduit or the like, enabling fluid to flow from the fluid container through the fluid reservoir to the aerosol generation device through the opening element.

The invention further provides a combination of the fluid reservoir and a primary fluid package, wherein the primary fluid package has at least one chamber containing a fluid therein. Herein, the term "primary fluid package" defines any type of package, container, blister, pouch, ampoule, vial or reservoir in which a fluid, such as a fluid containing a medicament, drug, substance or active compound, can be stored. The at least one chamber forms a fluid-tight space.

The primary fluid package can be made of various materials, for example, plastic, such as polypropylene, glass, ceramic, metal or other suitable materials. In particular, the primary fluid package may also consist of different or same materials in sections or in combinations, like sandwich materials. For example, a glass primary fluid package can be sealed with a plastic seal or different areas of the primary fluid package can be made of different plastics which are accordingly selected depending on their use at the corresponding primary fluid package areas.

The primary fluid package may be manufactured, for example, by a blow-fill-seal (BFS) process. In this way, the primary fluid package can be fabricated in a particularly simple and efficient manner.

The primary fluid package is configured so that it can be opened by removing a closure element from the package, thereby allowing the fluid packed in the at least one chamber to flow out of the package. The closure element may be configured so that it has to be torn or twisted off from the primary fluid package in order to open the package. In particular, the closure element may be a toggle closure or the like.

In use, the primary fluid package is opened and the fluid contained therein is filled into the fluid container or the fluid reservoir. Subsequently, if a separate fluid container is used, an adapter, such as those described above, may be attached to the container containing the fluid therein. The fluid container with the adapter attached thereto or the integral fluid reservoir, including the fluid container and the adapter as described above, is attached to the aerosol generation device for guiding the fluid from the fluid reservoir to the device. By providing the fluid reservoir and the primary fluid package in combination, it can be ensured that a suitable type of fluid reservoir is used for the fluid contained in the primary fluid package.

The primary fluid package may have two or more chambers, each chamber containing the same or a different fluid therein. Such a configuration is particularly advantageous for the case of multi-component fluids (drugs, medicaments, etc.), in which two or more fluid components have to be mixed or combined immediately before the aerosol treatment, for example, if the fluids in a mixed or combined state are not stable over a longer time period.

The primary fluid package may further comprise at least one chamber comprising a solid material (e.g., a solid medicament or drug), such as a dry powder, lyophilized powder, a granular material, a tablet or the like, which is to be mixed with the fluid or fluids contained in the remaining chamber or chambers.

The primary fluid package may be configured so that the plurality of chambers are sealed by a single closure element, such as a toggle closure. In this way, by removing the single closure element, all the chambers are opened, thus ensuring the correct mixing ratio of the different fluids and minimising the risk that one or more of the different fluids might be administered separately.

As has been discussed in detail above, the fluid reservoir of the invention is particularly advantageous for use with such multi-component fluids.

The fluid reservoir and the primary fluid package may be arranged together in a single package, for example, a pouch. The package may be made, for example, from plastic, such as polyethylene or the like: e.g., from a plastic bag.

By arranging the fluid reservoir and the primary fluid package together in a single package it can be ensured that the corresponding fluid reservoir and primary fluid package are used together in one aerosol treatment. Thus, the accidental use of a wrong fluid reservoir for a particular fluid or the use of the fluid in the primary fluid package without any fluid reservoir can be reliably avoided.

The fluid container, the primary fluid package and the adapter may be provided together, e.g., so that the fluid container, the primary fluid package and the adapter are arranged together in a single package, such as a pouch.

The invention further provides an aerosol generation device which is configured for use with the fluid reservoir. The aerosol generation device has an attachment portion for receiving the interface portion of the fluid reservoir. The aerosol generation device comprises the fluid reservoir.

The attachment portion may comprise an engagement section, such as a thread, threaded splines, a bayonet coupling or the like, for enabling attachment of the interface portion of the fluid reservoir thereto. The engagement section may comprise at least one detent element configured to lock the locking element of the fluid reservoir.

The attachment portion may have an override section. In particular, the attachment portion may be configured so that, after attachment of the fluid reservoir to the aerosol generation device, at least a part of the locking element of the fluid reservoir is arranged in the override section. In this state, the override section allows the fluid reservoir to rotate freely relative to the attachment portion, e.g., about the longitudinal axis of the fluid reservoir. However, this rotational movement does not induce any axial movement of the fluid reservoir relative to the attachment portion. Hence, the fluid reservoir is securely and initially non-detachably locked to the attachment portion.

The attachment portion of the aerosol generation device may have at least one detachment or release element, such as a wedge structure or the like, which automatically breaks the locking element when the fluid reservoir is detached, e.g., unscrewed, from the attachment portion of the aerosol generation device.

Further, the detachment or release element may comprise one or more openings, cut-outs, recesses or the like which are arranged so as to receive at least a part of the locking element of the fluid reservoir when the fluid reservoir is attached to the aerosol generation device. In this case, when the fluid reservoir is detached, e.g., unscrewed, from the attachment portion, the part of the locking element is retained by the one or more openings, cut-outs, recesses or the like, so that the locking element is automatically broken by the detachment or release element in the process of detaching the fluid reservoir from the aerosol generation device.

The aerosol generation device is configured so that a fluid can be supplied thereto only by use of the fluid reservoir. In particular, the aerosol generation device does not have an integral fluid reservoir for receiving a fluid to be nebulised.

The aerosol generation device of the invention may be any type of aerosol generation device, such as a nebuliser, an atomiser, such as a humidifier, a pneumatic nebuliser, a jet nebuliser, an electronic nebuliser, an ultrasonic nebuliser, an electrode-hydrodynamic nebuliser, an electrostatic nebuliser, a membrane nebuliser, a vibrating membrane nebuliser, e.g., an electronic vibrating membrane nebuliser, a humidifier/nebuliser for ventilation devices, or the like.

The aerosol generation device according to the invention provides the advantageous effects already described in detail above for the fluid reservoir of the invention. In particular, the aerosol generation device of the invention allows for a contamination of the generated aerosol to be reliably prevented, thereby ensuring an effective aerosol treatment.

The aerosol generation device may further have an opening element, such as a thorn, a hollow needle, a collar, a conduit or the like, for opening the interface portion of the fluid reservoir and guiding the fluid from the fluid reservoir into the interior of the aerosol generation device. The opening element may be provided with a sharp edge or tip portion, such as a blade element or the like, at a top portion thereof, in order to facilitate opening of the interface portion of the fluid reservoir and draining of the fluid from the fluid reservoir. Such a configuration is particularly advantageous for use with a fluid reservoir with an interface portion having a wall element sealing the end of the fluid reservoir, as described above.

The opening element of the aerosol generation device may be configured for opening a valve element, such as a ball valve, a valve diaphragm or the like, provided in the interface portion of the fluid reservoir for regulating fluid flow through the fluid reservoir into the aerosol generation device.

The opening element may have a substantially cylindrical shape. A conduit, channel or the like may be provided in the opening element for guiding fluid from the fluid reservoir into the interior of the aerosol generation device. The conduit or channel may have a substantially cylindrical shape. Alternatively, the opening element and/or the conduit or channel may have a rectangular, square, triangular or other polygonal cross-sectional shape. A substantially cylindrical shape of the opening element provides the advantage of enabling a particularly uniform opening of the fluid reservoir, thus allowing for a steady opening process. A substantially cylindrical shape of the conduit or channel offers the advantage of enabling a particularly homogeneous flow of the fluid through the opening element into the aerosol generation device.

The attachment portion of the aerosol generation device may be provided with a valve element, such as a ball valve or the like, for regulating fluid flow through the fluid reservoir into the interior of the aerosol generation device. In this way, the fluid flow into the device can be controlled with a particularly high degree of accuracy and precision, thereby ensuring a high aerosol dosage precision.

The aerosol generation device may further comprise a protective cap or lid for closing or sealing the attachment portion. In this way, a contamination of the aerosol generation device by ambient air entering the device can be reliably prevented when the device is not in use. The protective cap or lid may be attached to the aerosol generation device, e.g., by a hinge, integrally formed with the aerosol generation device or provided as a separate entity. The structure of the protective cap may be similar to that of the fluid reservoirs described above. In particular, the structure of an interface portion of the protective cap may be the same as that of the interface portions of these fluid reservoirs. The protective cap may differ from these fluid reservoirs in that it has a wall sealing the end of the protective cap so as to enable a reliable closing and sealing of the attachment portion.

The attachment portion of the aerosol generation device may have at least one opening (cut-out, recess) which is arranged so as to be closed by at least a part of the interface portion of the fluid reservoir after attachment of the fluid reservoir to the aerosol generation device. Further, the aerosol generation device may have a plurality of such openings which are arranged so as to be closed by at least a part of the interface portion after the fluid reservoir has been attached to the device. The at least one opening may be formed in a side wall and/or a bottom wall of the attachment portion.

By providing such an at least one opening in the attachment portion of the aerosol generation device, an accidental use or misuse of the device without the fluid reservoir in place can be particularly reliably prevented. Specifically, due to the presence of the at least one opening, the attachment portion of the aerosol generation device cannot store a fluid, since the fluid would drain from the at least one opening. The at least one opening in the attachment portion of the aerosol generation device may be formed as one or more gaps, spaces, holes or the like. By attaching the fluid reservoir to the aerosol generation device, the at least one opening is closed by at least a part of the interface portion of the fluid reservoir, thereby enabling the supply of fluid to the aerosol generation device.

The aerosol generation device of the invention comprises the fluid reservoir of the invention.

BRIEF DESCRIPTION OF THE DRAWINGS

Hereinafter, non-limiting examples of the invention are explained with reference to the drawings, in which:

FIGS. 1(a) to (d) show schematic views of a fluid reservoir according to a first embodiment of the present invention, wherein FIG. 1(a) is a perspective view of the fluid reservoir, FIG. 1(b) is a bottom view of the fluid reservoir, FIG. 1(c) is a top view of the fluid reservoir and FIG. 1(d) is a cross-sectional view of the fluid reservoir in a plane parallel to a direction of fluid flow through the fluid reservoir;

FIGS. 2(a) to (d) show schematic views of a portion of an aerosol generation device according to a first embodiment of the present invention, wherein FIG. 2(a) is a perspective view of the portion of the aerosol generation device, FIG. 2(b) is a cross-sectional view of the portion of the aerosol generation device in a plane parallel to a direction of aerosol flow, FIG. 2(c) is a side view of the portion of the aerosol generation device with the fluid reservoir of FIGS. 1(a) to (d) attached thereto and FIG. 2(d) is a cross-sectional view of the portion of the aerosol generation device with the fluid reservoir of FIGS. 1(a) to (d) attached thereto, in a plane parallel to the direction of aerosol flow;

FIGS. 3(a) to (d) show schematic views of a portion of an aerosol generation device according to a second embodiment of the present invention and a fluid reservoir according to a second embodiment of the present invention, wherein FIG. 3(a) is a perspective view of the fluid reservoir without cap, FIG. 3(b) is a perspective view of an attachment portion of the aerosol generation device, FIG. 3(c) is a perspective view of the portion of the aerosol generation device with the fluid reservoir attached thereto and FIG. 3(d) is a cross-sectional view of the portion of the aerosol generation device with the fluid reservoir attached thereto, in a plane parallel to the direction of aerosol flow;

FIGS. 4(a) to (d) show schematic views of a protective cap for closing or sealing an attachment portion of an aerosol generation device, wherein FIG. 4(a) is a perspective view of the protective cap, FIG. 4(b) is a bottom view of the protective cap, FIG. 4(c) is a top view of the protective cap and FIG. 4(d) is a cross-sectional view of the protective cap in a plane parallel to a longitudinal direction of the protective cap;

FIGS. 5(a) and (b) show schematic views of a portion of the aerosol generation device according to the first embodiment of the present invention shown in FIGS. 2(a) to (d) having the protective cap shown in FIGS. 4(a) to (d) attached thereto, wherein FIG. 5(a) is a perspective view of the portion of the aerosol generation device and FIG. 5(b) is a cross-sectional view of the portion of the aerosol generation device in a plane parallel to a direction of aerosol flow;

FIG. 6 shows a schematic view of an adapter and a primary fluid package which are arranged together in a pouch;

FIGS. 7(a) to (d) show schematic views illustrating the process of supplying fluid to an aerosol generation device according to a third embodiment of the present invention using the adapter and the primary fluid package of FIG. 6, wherein FIG. 7(a) illustrates the step of filling a fluid container with fluid from the primary fluid package, FIG. 7(b) is a perspective view of the fluid container with the adapter attached thereto, FIG. 7(c) illustrates the step of attaching the fluid reservoir, formed by the fluid container and the adapter, to the aerosol generation device and FIG. 7(d) is a cross-sectional view of the aerosol generation device with the fluid reservoir attached thereto in a plane parallel to a direction of aerosol flow; and FIGS. 8(a) and (b) show schematic views of a portion of an aerosol generation device according to a fourth embodiment of the present invention having a fluid reservoir according to a fourth embodiment of the present invention attached thereto, wherein FIG. 8(a) is a side view of the portion of the aerosol generation device and FIG. 8(b) is a cross-sectional view of the portion of the aerosol generation device in a plane parallel to a direction of aerosol flow.

DETAILED DESCRIPTION OF CURRENTLY PREFERRED EMBODIMENTS

Figure 1A:
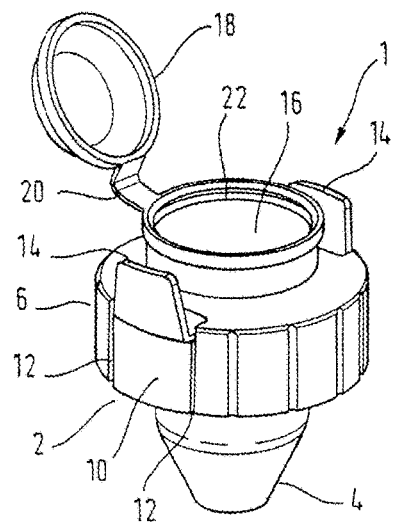
Figure 1B:
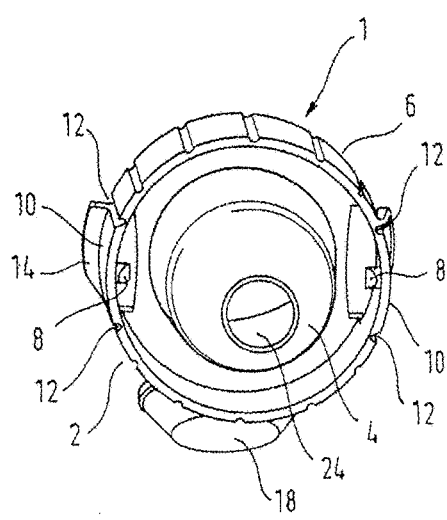
Figure 1C:
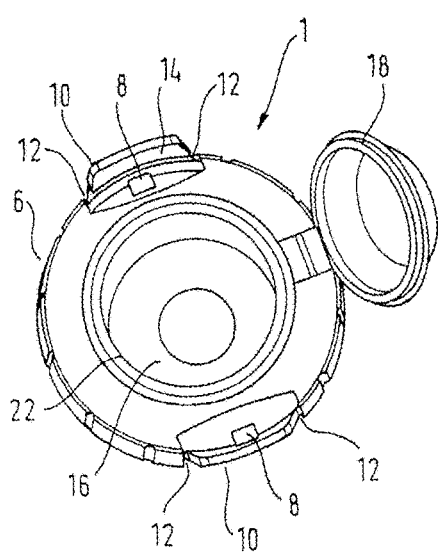
Figure 1D:
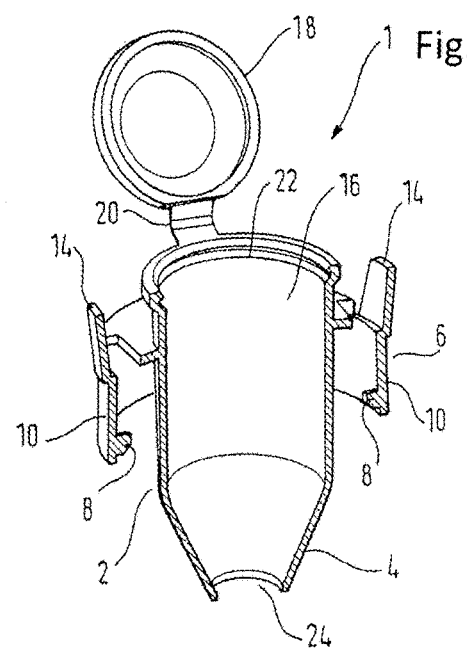

FIGS. 1(a) to (d) show schematic views of a fluid reservoir 1 according to a currently preferred first embodiment of the invention.

The fluid reservoir 1 shown in FIGS. 1(a) to 1(d) have an interface portion 2 arranged at an end 4 of the fluid reservoir 1 for attaching the fluid reservoir 1 to an aerosol generation device, which will be described later. The interface portion 2 comprises a collar 6 with a pair of pins 8, e.g., detent pins or locking pins, extending from an inner surface thereof. Each of portions 10 of the collar 6 on which the pins 8 are provided is connected to the remainder of the collar 6 through two weakened portions 12, facilitating removal of the collar portions 10 from the collar 6. Further, each of the collar portions 10 is integrally formed with a flap or tab 14 extending upwards from the collar portions 10 in an axial direction of the fluid reservoir 1, i.e., in a direction of fluid flow in the fluid reservoir 1.

The pins 8 provided on the collar 6 of the fluid reservoir 1 can be brought into engagement with a corresponding engagement section, such as a thread, threaded splines, a bayonet coupling or the like, provided on an attachment portion of the aerosol generation device so as to initially non-detachably lock the fluid reservoir 1 to the aerosol generation device after attachment of the fluid reservoir 1 thereto, as will be described in detail below.

The portions 10 of the collar 6 on which the pins 8 are provided can be removed from the collar 6 by pulling the flaps or tabs 14 outwards in a radial direction of the fluid reservoir 1, thereby breaking or tearing the weakened portions 12. In this way, the collar portions 10 and thus also the pins 8 can be removed from the collar 6, thereby breaking the lock and enabling detachment of the fluid reservoir 1 from the aerosol generation device. Hence, the pins 8, the collar portions 10, the weakened portions 12 and the flaps or tabs 14 in combination form a breakable locking element.

The fluid reservoir 1 according to the first embodiment of the invention is integrally formed with a fluid container 16. The fluid container 16 comprises a lid element 18 for sealing the fluid container 16. The lid element 18 is connected to a top portion of the fluid reservoir 1 by a resilient hinge 20. The lid element 18 can be secured to an opening 22 of the fluid container 16 by a snap fit or the like, thereby sealing the fluid container 16.

The end 4 of the fluid reservoir 1 has an opening 24 which is suitable for receiving a valve element (not shown), such as a ball valve, a valve diaphragm or the like, for regulating fluid flow through the fluid reservoir 1 into the aerosol generation device. Alternatively, the opening 24 provided at the end 4 of the fluid reservoir 1 may remain open.

Next, the use of the fluid reservoir 1 for supplying a fluid to an aerosol generation device is described with reference to FIGS. 2(a) to (d), which show schematic views of a portion 50 of an aerosol generation device according to a currently preferred first embodiment of the invention.

The aerosol generation device has an attachment portion 52 for receiving the interface portion 2 of the fluid reservoir 1. The attachment portion 52 has an engagement section 54, such as a thread, threaded splines or a bayonet coupling, configured to receive the pins 8 provided on the interface portion 2 of the fluid reservoir 1.

Figure 2A:
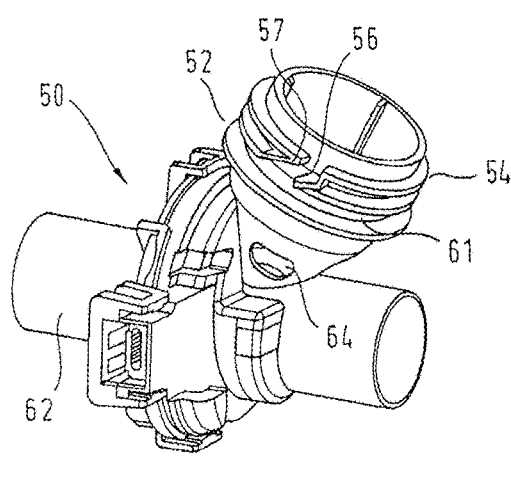

The attachment portion 52 has an override section 56. As is shown in FIG. 2(a), the override section 56 is formed by a portion of the engagement section 54 in which a threaded spline passes into a circumferential groove 61 extending along the circumference of the attachment portion 52. In particular, the engagement section 54 is configured so that, when screwing the fluid reservoir 1 onto the attachment portion 52, the pins 8 of the fluid reservoir 1 are guided by a guiding groove 57 of the engagement section 54 into the circumferential groove 61. Once the pins 8 have entered into the circumferential groove 61, the fluid reservoir 1 is freely rotatable relative to the attachment portion 52 about the longitudinal axis of the fluid reservoir 1, but this rotational movement does not induce any axial movement of the fluid reservoir 1 relative to the attachment portion 52. Hence, the fluid reservoir 1 is securely and initially non-detachably locked to the attachment portion 52.

The aerosol generation device of the first embodiment, a portion 50 of which is shown in FIGS. 2(a) to (d), is a vibrating membrane nebuliser. The device comprises a membrane space 58 in which the membrane 59 is arranged. Fluid is guided from the attachment portion 52 through a conduit or channel 60 to the membrane 59, where it is nebulised so as to generate an aerosol. The generated aerosol is supplied to a patient via a conduit or channel 62.

In one embodiment, the conduit or channel 62 is coupled to a ventilator tube system that is connected to the patient. In an alternative embodiment, the conduit or channel 62 may be connected to or formed as a mouthpiece or a face mask or a nose mask or an endotracheal tube with or without a valve to connect the aerosol generation device directly to a patient.

Figure 2B:
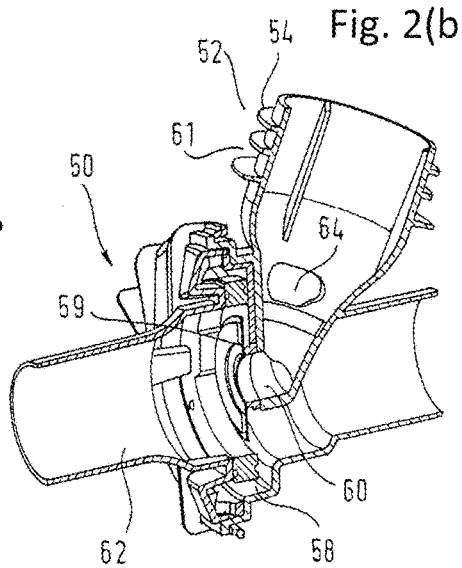
Figure 2C:
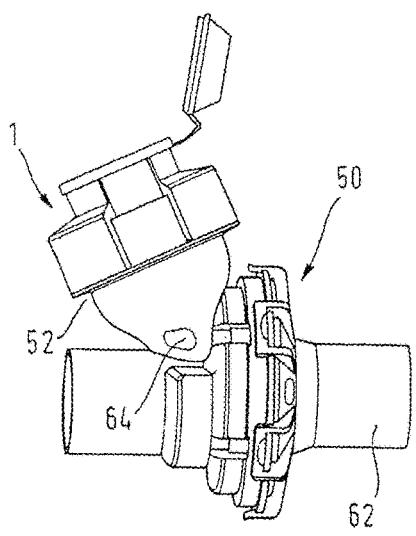
Figure 2D:
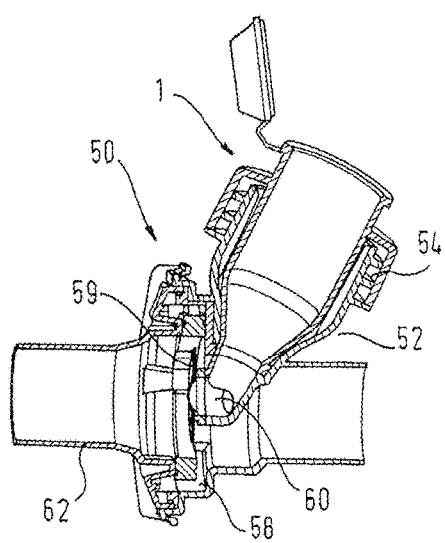

The attachment portion 52 of the aerosol generation device has at least one opening 64 provided in the side wall or the bottom wall thereof, as shown in FIGS. 2(a) to (c). This opening 64 prevents a direct filling of the attachment portion 52 with a fluid, since fluid supplied directly to the attachment portion 52 would flow out of the device through the at least one opening 64. Hence, no fluid can be stored in the attachment portion 52. In this way, a use of the aerosol generation device without the fluid reservoir 1 can be reliably prevented.

In the following, the steps for supplying a fluid to the aerosol generation device using the fluid reservoir 1 of the first embodiment with and without a valve element provided in the opening 24 are described.

If the opening 24 of the fluid reservoir 1 is left open, i.e., no valve element is provided in the opening 24, the fluid reservoir 1 is first attached to the attachment portion 52 of the aerosol generation device.

Specifically, the pins 8 of the interface portion 2 of the fluid reservoir 1 are inserted into the engagement section 54 of the attachment portion 52 and the fluid reservoir 1 is screwed onto the attachment portion 52 (FIGS. 2(c) and (d)). Once the pins 8 have entered into the circumferential groove 61 of the override section 56 of the engagement section 54, the override section 56 prevents the pins 8 from moving upwards in the axial direction of the attachment portion 52, so that the fluid reservoir 1 cannot be unscrewed from the attachment portion 52. In this state, the pins 8 can move freely in the circumferential groove 61, so that the fluid reservoir 1 is freely rotatable relative to the attachment portion 52 about the longitudinal axis of the fluid reservoir 1. However, this rotational movement does not induce any axial movement of the fluid reservoir 1 relative to the attachment portion 52. In this way, the fluid reservoir 1 is non-detachably locked to the aerosol generation device.

After attachment of the fluid reservoir 1 to the aerosol generation device, the opening 64 of the attachment portion 52 is closed by a lower part of the interface portion 2 of the fluid reservoir 1 (FIGS. 2(c) and (d)), thereby forming a fluid-tight fluid space and enabling the supply of fluid to the membrane 59 of the aerosol generation device.

After the fluid reservoir 1 has been attached to the aerosol generation device, as shown in FIGS. 2(c) and (d), a fluid or a mixture of fluids is filled into the fluid container 16 through the opening 22. Subsequently, the fluid container 16 is sealed by closing the opening 22 with the lid element 18. The fluid contained in the fluid container 16 is guided to the membrane 59 through the conduit or channel 60 of the aerosol generation device and nebulised by the vibrating membrane 59.

After the aerosol treatment has been finished and the fluid in the fluid container 16 has been used up, the fluid reservoir 1 is removed from the attachment portion 52 of the aerosol generation device. As has been detailed above, the pins 8 of the fluid reservoir 1 and the override section 56 of the attachment portion 52 prevent the fluid reservoir 1 from being unscrewed, so that the fluid reservoir 1 is locked to the aerosol generation device. Hence, in order to detach the fluid reservoir 1 from the device, the portions 10 of the collar 6 of the fluid reservoir 1 which have the pins 8 provided thereon have to be manually removed from the collar 6 by pulling the flaps or tabs 14 radially outward, thereby breaking or tearing the weakened portions 12.

Once the collar portions 10 with the pins 8 have been removed from the collar 6, the fluid reservoir 1 can be lifted from the attachment portion 52. Since, after detachment of the fluid reservoir 1 from the attachment portion 52, the fluid reservoir 1 no longer has the pins 8, it cannot be reattached to the attachment portion 52. Hence, the fluid reservoir 1 is destroyed, i.e., rendered unusable, so that an accidental reuse thereof is reliably prevented.

If the opening 24 of the fluid reservoir 1 is provided with a valve element, the supply of fluid to the aerosol generation device comprises the following steps.

The valve element is configured so that it is closed in its normal state, i.e., if no external force is applied thereto, so as to seal the opening 24 of the end 4 of the fluid reservoir 1. Hence, the fluid container 16 can be filled with a fluid or a mixture of fluids prior to the attachment of the fluid reservoir 1 to the aerosol generation device. After the fluid container 16 has been filled with the fluid or the mixture of fluids, the fluid container 16 is sealed by closing the opening 22 with the lid element 18.

Subsequently, the fluid reservoir 1 having the fluid or mixture of fluids contained therein is attached to the attachment portion 52 of the aerosol generation device in the same manner as described above, i.e., by screwing the fluid reservoir 1 onto the attachment portion 52.

Figure 7A:
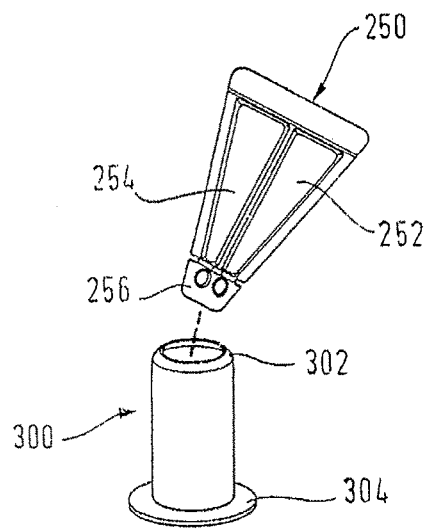

The screwing motion of the fluid reservoir 1 causes a downward movement of the fluid reservoir 1 in the axial direction of the fluid reservoir 1. This downward movement brings the valve element provided in the opening 24 of the fluid reservoir 1 into contact with an opening element (not shown in FIG. 2; see FIGS. 7(c) and 7(d)), such as a thorn, a hollow needle, a collar, a conduit or the like, provided in the aerosol generation device and presses the valve element onto the opening element, whereby the opening element opens the valve element.

Once the valve element has been opened in this way, fluid flows from the fluid container 16 through the conduit or channel 60 to the membrane 59 provided in the membrane space 58 where it is nebulised.

After the aerosol treatment has been finished, the fluid reservoir 1 is detached from the attachment portion 52 of the aerosol generation device in the same manner as described above, i.e., by removing the collar portions 10 with the pins 8 and lifting the fluid reservoir 1 from the attachment portion 52.

FIGS. 3(a) to (d) show schematic views of a portion 160 of an aerosol generation device according to a currently preferred second embodiment of the present invention and a fluid reservoir 100 according to a currently preferred second embodiment of the present invention.

The structure of the interface portion 102 of the fluid reservoir 100 according to the second embodiment is identical to that of the interface portion 2 of the fluid reservoir 1 of the first embodiment shown in FIG. 1. Therefore, a detailed description thereof is omitted.

The fluid reservoir 100 differs from the fluid reservoir 1 in the shape of the flaps or tabs 114. The flaps or tabs 114 are arranged at a top section of collar portions 110 on which pins (not shown in FIGS. 3(a) to 3(d); see FIGS. 1(b) and (c)) are provided in the same manner as for the fluid reservoir 1 of the first embodiment and the flaps or tabs 114 are configured so as to extend in a radially outward direction.

Further, the fluid reservoir 100 differs from the fluid reservoir 1 in that the lid element 18 is replaced by a cap 118. The cap 118 can be securely attached to an engagement portion 108 arranged on the fluid reservoir 100 at a position opposite to the end 104 of the fluid reservoir 100. By attaching the cap 118 to the engagement portion 108, a fluid container 116 which is integrally formed with the fluid reservoir 100 can be reliably sealed.

Figure 3A:
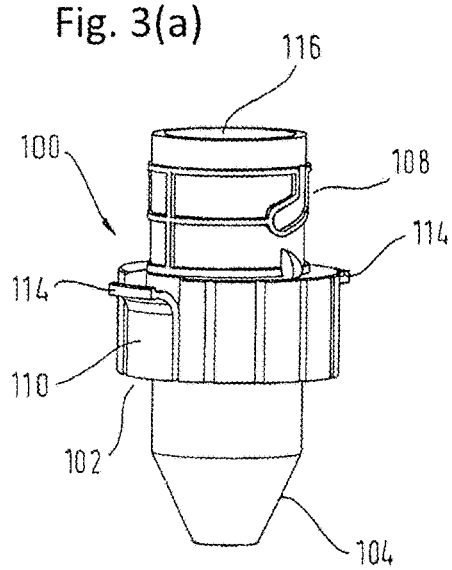
Figure 3B:
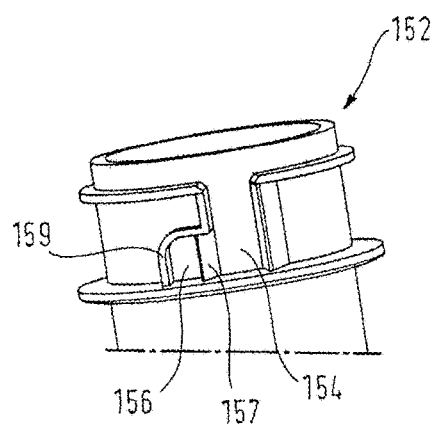
Figure 3C:
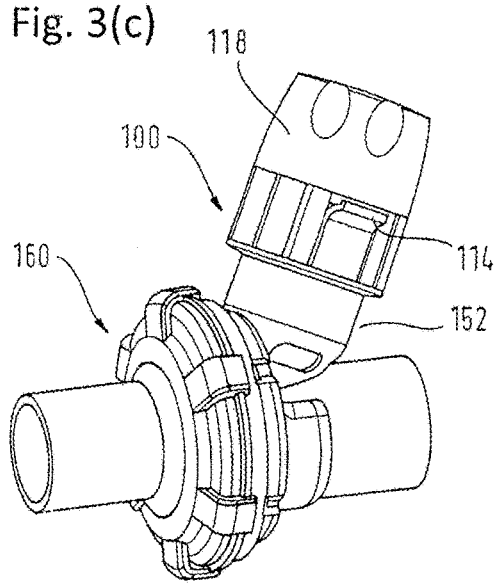
Figure 3D:
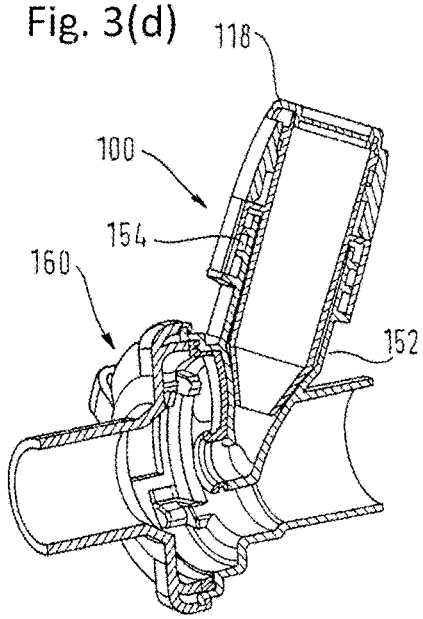
Figure 4A:
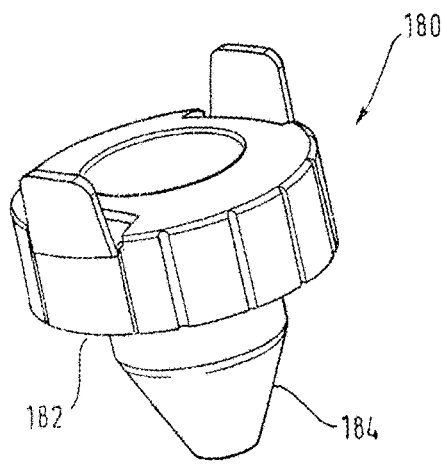
Figure 4B:
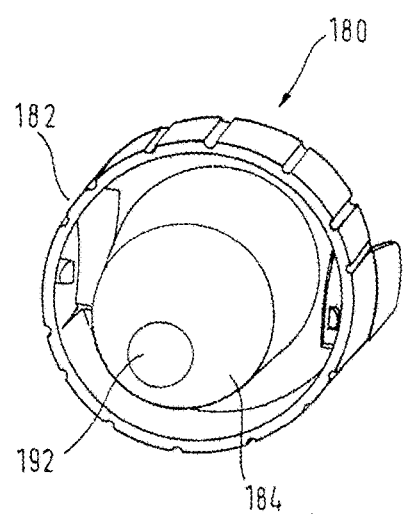
Figure 4C:
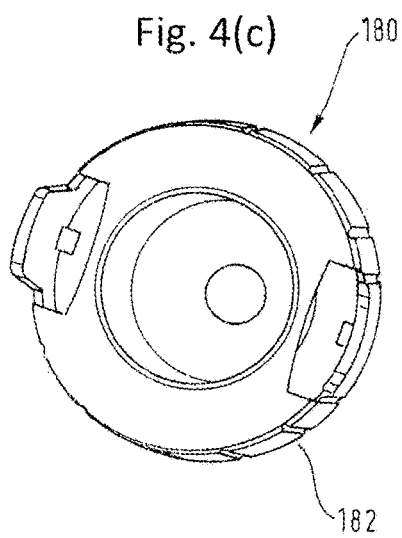
Figure 4D:
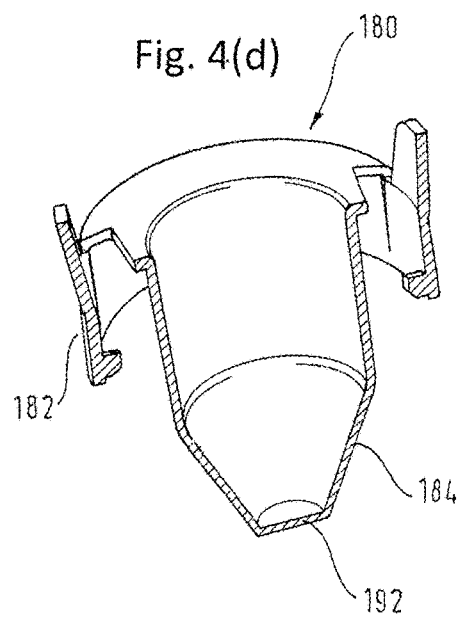

The aerosol generation device according to the second embodiment differs from the aerosol generation device according to the first embodiment in that the engagement section 154 of the attachment portion 152 has two detent sections 156 instead of the override section 56. The detent sections 156 are configured to lock the pins of the fluid reservoir 100 in their positions. One of the two detent sections 156 is shown in FIG. 3(b). The other of the two detent sections 156 is arranged on the attachment portion 152 in a position radially opposite to the detent section 156 shown in FIG. 3(b).

Each detent section 156 comprises a wedge-shaped element 157 and a stop element 159 which is arranged at a position opposite to the wedge-shaped element 157 in a circumferential direction of the attachment portion 152 (FIG. 3(b)). Between the wedge-shaped element 157 and the stop element 159, a space for receiving and locking a pin of the fluid reservoir 100 is formed.

Specifically, when attaching the fluid reservoir 100 to the attachment portion 152, the pins of the fluid reservoir 100 are guided past the wedge-shaped elements 157. The wedge-shaped elements 157 are configured so that they allow for a movement of the pins over the elements 157 in the attachment direction but prevent a movement of the pins in a direction opposite thereto, once the pins have moved past the elements 157. In this way, the pins are locked in their positions by the wedge-shaped elements 157 and the stop elements 159.

In this state, the pins of the fluid reservoir 100 and the detent sections 156 of the attachment portion 152 prevent the fluid reservoir 100 from being detached from the aerosol generation device, so that the fluid reservoir 100 is initially non-detachably locked to the device. Hence, in order to detach the fluid reservoir 100 from the device, the collar portions 110 of the fluid reservoir 100 which have the pins provided thereon have to be manually removed by pulling the flaps or tabs 114 radially outward, in the same manner as described above for the fluid reservoir 1 of the first embodiment.

Once the collar portions 110 with the pins have been removed, the fluid reservoir 100 can be lifted from the attachment portion 152. Since, after detachment of the fluid reservoir 100 from the attachment portion 152, the fluid reservoir 100 no longer has the pins, it cannot be reattached to the attachment portion 152. Hence, the fluid reservoir 100 is destroyed, i.e., rendered unusable, so that an accidental reuse thereof is reliably prevented.

The engagement section 154 of the attachment portion 152 may have one or more detent sections 156. Preferably, the number of detent sections 156 equals the number of pins provided on the fluid reservoir 100.

The remaining details concerning both the structure and the use of the fluid reservoir 100 and the aerosol generation device of the second embodiment are the same as those of the fluid reservoir 1 and the aerosol generation device of the first embodiment. Therefore, a detailed description thereof is omitted.

FIGS. 4(a) to 4(d) show a protective cap 180 for closing or sealing an attachment portion of an aerosol generation device, e.g., the aerosol generation device of the first or the second embodiment. By attaching the protective cap 180 to the attachment portion, a contamination of the aerosol generation device by ambient air entering into the device can be reliably prevented when the device is not in use.

The structure of the protective cap 180 is similar to that of the fluid reservoir 1 according to the first embodiment of the present invention, as will be detailed in the following.

In particular, the structure of an interface portion 182 of the protective cap 180 is identical to that of the interface portion 2 of the fluid reservoir 1 of the first embodiment shown in FIGS. 1(a) to 1(d). Therefore, a detailed description thereof is omitted. The protective cap 180 differs from the fluid reservoir 1 in that it has a wall 192 sealing the end 184 of the protective cap 180 and does not have a fluid reservoir integrally formed therewith.

The protective cap 180 is attached to the aerosol generation device and detached therefrom in the same manner as described above for the fluid reservoir 1. Schematic views of the protective cap 180 attached to the aerosol generation device of the first embodiment are presented in FIGS. 5(a) and 5(b). As is shown in FIG. 5(b), the end 184 of the protective cap 180 having the wall 192 provided thereon closes and seals the attachment portion 52 of the aerosol generation device. In this way, ambient air is prohibited from entering into the device, so that a contamination of the device and thus also the generated aerosol can be reliably prevented when the device is not in use.

FIG. 6 shows a schematic view of a pouch 150 made of plastic, such as polyethylene, containing an adapter 200 of a fluid reservoir according to a currently preferred third embodiment of the present invention and a primary fluid package 250.

The structure of the adapter 200 is similar to that of the lower portion of the fluid reservoir 1 (i.e., the portion of the fluid reservoir 1 closer to the end 4) according to the first embodiment shown in FIG. 1, as will be explained in detail below.

The structure of an interface portion 202 of the adapter 200 for attaching the adapter 200 to an aerosol generation device is substantially identical to that of the interface portion 2 of the fluid reservoir 1 of the first embodiment. Therefore, a detailed description thereof is omitted.

The adapter 200 differs from the lower portion of the fluid reservoir 1 in the arrangement and the shape of the flaps or tabs 214. The flaps or tabs 214 are arranged at a bottom section of collar portions 210 on which pins (not shown in FIG. 6; see FIGS. 1(b) and (c)) are provided in the same manner as for the fluid reservoir 1 of the first embodiment and the flaps or tabs 214 are configured so as to extend in a radially outward direction.

Figure 7B:
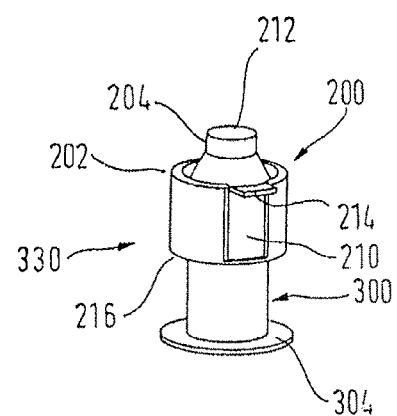

Further, the adapter 200 differs from the lower portion of the fluid reservoir 1 in that it has a wall element 212 (FIG. 7(b)) sealing an end 204 of the adapter 200. The wall element 212 has at least one weakened portion (not shown) facilitating at least partial breaking of the wall element 212. In use of the adapter 200, the wall element 212 is at least partially broken by an opening element (see FIGS. 7(c) and (d)), such as a thorn, a hollow needle, a collar, a conduit or the like, provided in the aerosol generation device.

The adapter 200 does not have a fluid container integrally formed therewith, as will be explained in detail below with reference to FIGS. 7(a) to 7(d). The adapter 200 is attachable to a fluid container 300, as is shown in FIGS. 7(a) and (b). The adapter 200 has another interface portion 216 arranged at another end of the adapter 200, opposite the end 204 sealed by the wall element 212, for attaching the adapter 200 to the fluid container 300. For example, the other interface portion 216 may be provided with a tapping, a thread, threaded splines, a bayonet coupling or the like (not shown) for engagement with a corresponding structure, such as a thread or threaded splines, provided on the fluid container 300. In this case, the other interface portion 216 of the adapter 200 can be screwed onto the fluid container 300.

The other interface portion 216 and/or the corresponding structure on the fluid container 300 may be provided with a valve element for regulating fluid flow through the fluid reservoir into the aerosol generation device. The valve element may be configured so that it can be opened by a corresponding opening element provided in the aerosol generation device. The valve element may be configured so that it is normally, i.e., if no external force is applied thereto, in a closed state. The valve element may be, for example, a ball valve, a valve diaphragm or the like.

The fluid reservoirs 1, 100 and the adapter 200 are made of plastic, e.g., polypropylene, and are each formed as a single piece by injection moulding.

The primary fluid package 250 is made of plastic, such as polypropylene, and is fabricated by a blow-fill-seal method.

As is schematically illustrated in FIG. 6, the pouch 150 is configured so as to be at least partially transparent.

The primary fluid package 250 has two separate chambers 252, 254, each of which contains a different fluid therein. Specifically, the two fluids contained in the chambers 252, 254 of the primary fluid package 250 form part of a multi-component fluid, i.e., the two fluids have to be combined or mixed immediately before the aerosol treatment.

The chambers 252, 254 are sealed by a single, common closure element 256, such as a toggle closure. In this way, the correct mixing ratio of the two fluids can be ensured and the risk of the fluids being administered separately can be minimised.

Providing the adapter 200 and the primary fluid package 250 together in a single pouch 150 minimises the risk that the primary fluid package 250 is used without a suitable adapter or fluid reservoir.

In the following, the use of the adapter 200 and the primary fluid package 250 shown in FIG. 6 for supplying a mixture of fluids to an aerosol generation device according to a currently preferred third embodiment of the present invention is described in detail with reference to FIGS. 7(a) to (d).

Figure 7C:
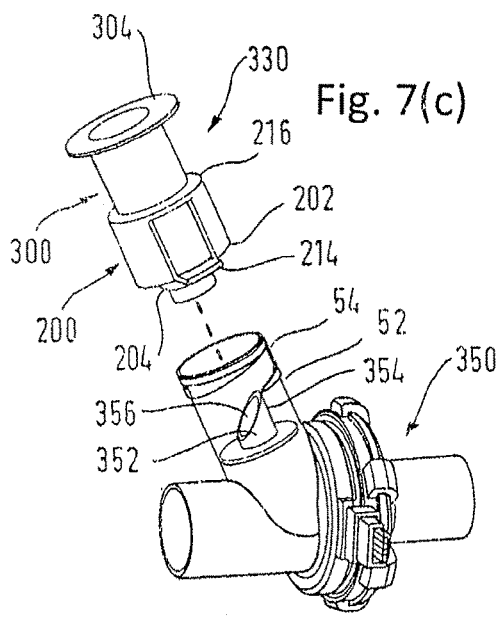
Figure 7D:
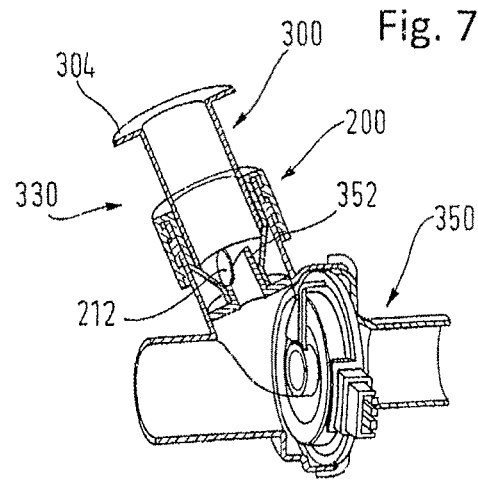

The aerosol generation device according to the third embodiment, a portion 350 of which is shown in FIGS. 7(c)

and (*d*), is substantially identical in its structure with the aerosol generation device according to the first embodiment. Therefore, a detailed description thereof is omitted and the same reference signs as for the aerosol generation device of the first embodiment are used.

The aerosol generation device of the third embodiment has an opening element 352 provided in the attachment portion 52 with an inclined top surface 354, forming a sharp tip for facilitating opening of the wall element 212 of the adapter 200, and an inner conduit 356 for guiding fluid from the adapter 200 into the interior of the aerosol generation device.

In the process of supplying fluid to the aerosol generation device, the adapter 200 and the primary fluid package 250 are taken out of the pouch 150. Subsequently, the closure element 256 is removed from the primary fluid package 250, thereby opening the chambers 252, 254 of the primary fluid package 250, and the fluids contained in these chambers 252, 254 are filled into the fluid container 300, thereby mixing the fluids (FIG. 7(*a*)).

The fluid container 300 has an attachment section 302, for example comprising a thread or threaded splines, for receiving the other interface portion 216 of the adapter 200.

Further, the fluid container 300 comprises a base portion 304 which allows for the reservoir 300 to be stably placed on a flat surface. Hence, the fluid container 300 can be filled with fluid in a particularly simple and convenient manner, by placing the container 300 on a table or the like and filling in the fluid from the top of the primary fluid package 250.

After the two fluids have been filled into the fluid container 300, the adapter 200 is attached to the fluid container 300 by bringing the other interface portion 216 of the adapter 200 into engagement with the attachment section 302 of the fluid container 300, e.g., by screwing the other interface portion 216 of the adapter 200 onto the attachment section 302 (FIG. 7(*b*)). In this way, the adapter 200 and the fluid container 300 together form the fluid reservoir 330 of the third embodiment and provide a fluid-tight space containing the mixture of fluids.

Subsequently, the fluid reservoir 330, i.e., the adapter 200 having the fluid container 300 attached thereto, is attached to the attachment portion 52 of the aerosol generation device. Specifically, the pins of the interface portion 202 of the adapter 200 are inserted into the engagement section 54 of the attachment portion 52 and the adapter 200 is screwed onto the attachment portion 52 (FIGS. 7(*c*) and (*d*)).

This screwing motion causes a downward movement of the adapter 200 in its axial direction, pressing the wall element 212 against the inclined top surface 354 of the opening element 352. The inclined top surface 354 of the opening element 352 at least partially breaks the wall element 212, so that the mixture of fluids contained in the fluid container 300 can flow through the adapter 200 into the conduit 356 of the opening element 352 and towards the membrane (not shown) of the aerosol generation device (FIG. 7(*d*)).

In the attached state of the adapter 200, the adapter 200, and thus the fluid reservoir 330, is initially non-detachably locked to the aerosol generation device by the pins of the interface portion 202 cooperating with the override section 56 of the attachment portion 52. In order to detach the fluid reservoir 330 from the aerosol generation device, the collar portions 210 on which the pins are provided have to be removed from the adapter 200 by pulling the flaps or tabs 214 in the radially outward direction. After the collar portions 210 have been removed, the fluid reservoir 330 can be lifted from the attachment portion 52.

After detachment of the fluid reservoir 330 from the aerosol generation device, the adapter 200 no longer comprises the pins. Hence, the adapter 200 and thus the fluid reservoir 330 is destroyed, i.e., rendered unusable. Therefore, an accidental reuse of the adapter 200 can be reliably prevented, thus ensuring an effective aerosol treatment.

As has been detailed above, the fluid reservoirs 1, 100, 330 and the adapter 200 have an interface portion 2, 102, 202 with a locking element 8, 10, 110, 210, 12, 14, 114, 214 which is configured so that it has to be manually broken before detachment of the fluid reservoir 1, 100, 330 from the aerosol generation device.

However, alternatively, the fluid reservoirs 1, 100, 330 and the adapter 200 may have a locking element which is configured so that the locking element is automatically broken when detaching the fluid reservoir 1, 100, 330 from the aerosol generation device. In this case, the attachment portion 52 of the aerosol generation device may have at least one detachment or release element, such as a wedge structure or the like, which automatically breaks the locking element when the fluid reservoir 1, 100, 330 is detached, e.g., unscrewed, from the attachment portion 52.

Further, the detachment or release element may comprise one or more openings, cut-outs or recesses which are arranged so as to receive the flaps or tabs 14, 114, 214 of the fluid reservoir 1, 100, 330 when the fluid reservoir 1, 100, 330 is attached to the aerosol generation device. In this case, when the fluid reservoir 1, 100, 330 is detached, e.g., unscrewed, from the attachment portion 52, the flaps or tabs 14, 114, 214 are retained by the one or more openings, cut-outs or recesses, so that the flaps or tabs 14, 114, 214 are automatically pulled by the detachment or release element in the process of detaching the fluid reservoir 1, 100, 330 from the aerosol generation device, thereby automatically removing the collar portions 10, 110, 210 from the interface portion 2, 102, 202.

The fluid reservoirs 1, 100, 330 the adapter 200 and/or the fluid container 300 may be provided with sealing elements, such as sealing rings or the like, e.g., provided in the interface portions 2, 102, 202, 216 of the fluid reservoir 1, 100, 330 and/or the adapter 200 and/or the attachment section 302 of the fluid container 300, in order to further improve their fluid-tightness.

Figure 8A:
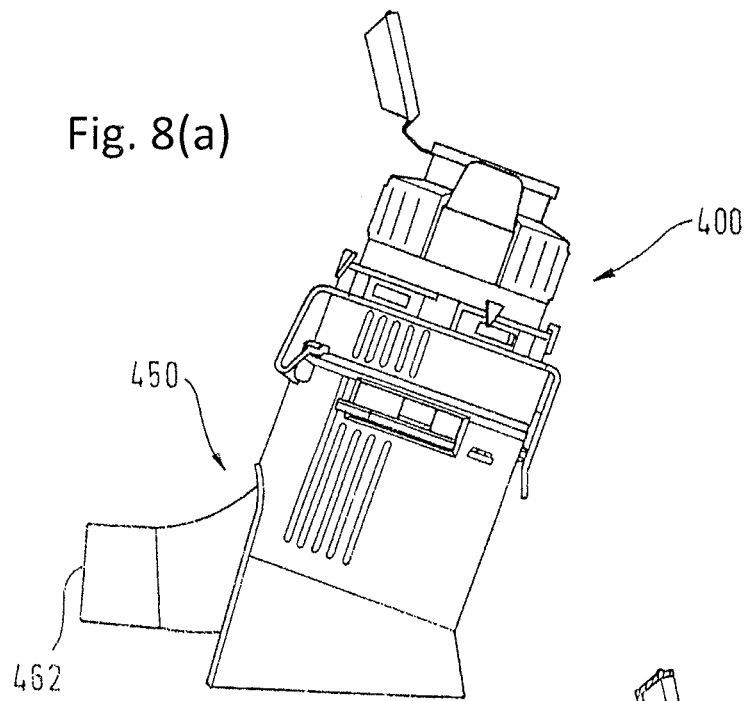
Figure 8B:
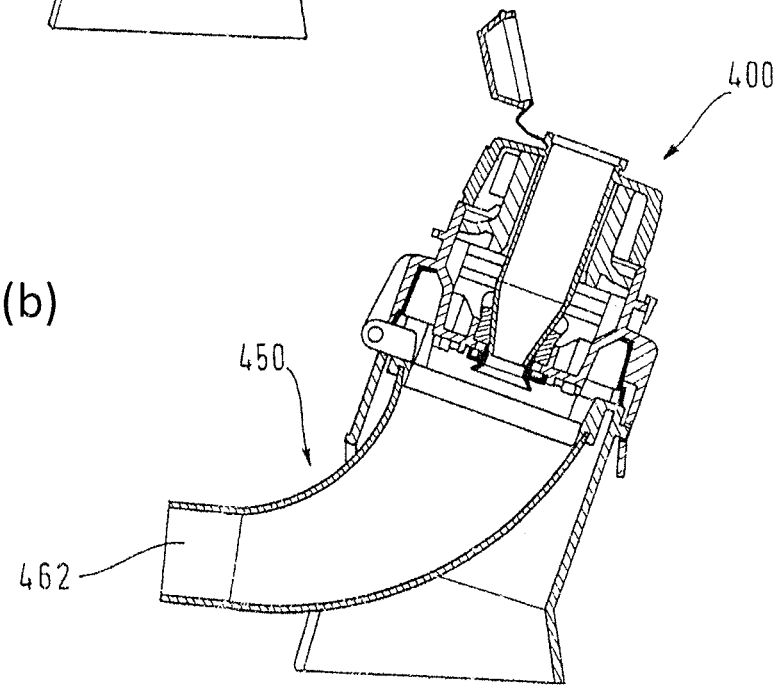

FIGS. 8(*a*) and (*b*) show schematic views of a portion 450 of an aerosol generation device according to a currently preferred fourth embodiment of the present invention having a fluid reservoir 400 according to a currently preferred fourth embodiment of the present invention attached thereto.

The fluid reservoir 400 of the fourth embodiment differs from the fluid reservoir 1 of the first embodiment in that it has a wall element, such as that of the adapter 200 shown in FIG. 7(*b*), sealing the end of the fluid reservoir 400. The wall element has at least one weakened portion facilitating at least partial breaking of the wall element. In use of the fluid reservoir 400, the wall element is at least partially broken by an opening element (as shown in FIGS. 7(*c*) and (*d*)), such as a thorn, a hollow needle, a collar, a conduit or the like, provided in the aerosol generation device.

The aerosol generation device of the fourth embodiment has an opening element, such as the opening element 352 of the aerosol generation device of the third embodiment shown in FIGS. 7(*c*) and (*d*), for facilitating opening of the wall element of the fluid reservoir 400 and guiding fluid from the fluid reservoir 400 into the interior of the aerosol generation device.

The aerosol generation device of the fourth embodiment differs from the aerosol generation device of the third embodiment in that it is a hand-held device which can be held by a patient during an aerosol treatment. Hence, the aerosol generation device of the fourth embodiment allows for a particularly high degree of mobility.

In the aerosol treatment, a generated aerosol is supplied to the patient via a conduit or channel 462. The conduit or channel 462 may be coupled to a tube or pipe that is connected to the patient. Alternatively, the conduit or channel 462 may be connected to or formed as a mouthpiece or a face mask or a nose mask or an endotracheal tube with or without a valve to connect the aerosol generation device directly to the patient.

The invention claimed is:

1. A fluid reservoir which is attachable to an aerosol generation device for guiding a fluid to the aerosol generation device, the fluid reservoir comprising:
    a fluid container; and
    an interface portion affixed to the fluid container and configured to attach the fluid container to the aerosol generation device, wherein
    the interface portion includes a locking element configured to lock the fluid container to the aerosol generation device after attachment of the fluid container to the aerosol generation device, and
    the interface portion includes a weakened portion that is breakable to enable detachment of the fluid container from the aerosol generation device.

2. The fluid reservoir according to claim 1, further comprising an adapter, wherein the adapter comprises the interface portion.

3. The fluid reservoir according to claim 1, wherein the fluid container is formed integrally with the interface portion.

4. The fluid reservoir according to claim 1, further comprising a lid element for sealing the fluid container.

5. The fluid reservoir according to claim 4, wherein the lid element is configured so that, after sealing the fluid container, the lid element cannot be detached from its sealing position without breaking the lid element or the fluid container.

6. The fluid reservoir according to claim 1, wherein the locking element is configured so that it has to be manually broken before detachment of the fluid container from the aerosol generation device.

7. The fluid reservoir according to claim 1, wherein the locking element is configured so that the locking element is broken when detaching the fluid container from the aerosol generation device.

8. The fluid reservoir according to claim 1, wherein the interface portion of the fluid reservoir further has a valve element for sealing an end of the fluid container and regulating the fluid flow to the aerosol generation device.

9. The fluid reservoir according to claim 1, wherein the interface portion of the fluid reservoir further has a wall element sealing an end of the fluid container, and
    the wall element has at least one weakened portion facilitating at least partial breaking of the wall element.

10. A combination of the fluid reservoir according to claim 1 and a primary fluid package, wherein
    the primary fluid package has at least one chamber containing a fluid therein.

11. The combination according to claim 10, wherein the fluid reservoir and the primary fluid package are arranged together in a single package.

12. An aerosol generation device which is configured for use with the fluid reservoir according to claim 1, the aerosol generation device having:
    an attachment portion for receiving the interface portion of the fluid reservoir, wherein
    the aerosol generation device comprises the fluid reservoir according to claim 1.

13. The aerosol generation device according to claim 12, further having an opening element for opening the interface portion of the fluid reservoir and guiding the fluid from the fluid container to the aerosol generation device.

14. The aerosol generation device according to claim 12, wherein the attachment portion has at least one opening, and
    the at least one opening is arranged so as to be closed by the interface portion of the fluid reservoir after attachment of the fluid container to the aerosol generation device.

* * * * *